United States Patent [19]
Jovanović

[11] 4,082,510
[45] Apr. 4, 1978

[54] AUTOCLAVE

[76] Inventor: Dragomir Jovanović, 6, Impasse Jean-Moulin, Pont-de-Claix, France

[21] Appl. No.: 817,422

[22] Filed: Jul. 20, 1977

[30] Foreign Application Priority Data

Jul. 21, 1976  France .................................. 76 23096

[51] Int. Cl.² .......................... A61L 3/00; A23L 3/00
[52] U.S. Cl. .......................................... 21/96; 21/98; 99/367; 99/483; 220/240; 220/316
[58] Field of Search ................... 21/96, 97, 98, 94, 95; 23/290; 220/240, 316; 126/348, 369; 99/371, 359, 367, 467, 483; 426/403, 407, 511

[56] References Cited

U.S. PATENT DOCUMENTS

| 3,511,593 | 5/1970 | Thomas et al. ....................... 21/96 X |
| 3,826,612 | 7/1974 | Black .................................... 21/96 X |
| 3,980,431 | 9/1976 | Anderson ................................ 21/94 |
| 3,983,260 | 9/1976 | Ford .................................. 99/359 X |

*Primary Examiner*—Morris O. Wolk
*Assistant Examiner*—Roger F. Phillips
*Attorney, Agent, or Firm*—Karl F. Ross

[57] ABSTRACT

An autoclave, to be used as a pressure cooker or a sterilizer, has a cylindrical vessel centered on a horizontal axis with open ends rimmed by radially inwardly projecting shoulders reinforced by rings with axially outwardly converging resilient external flanges and axially inwardly diverging resilient internal flanges forming small-diameter outer annular seats and large-diameter inner annular seats. A carriage, axially slidable along a base supporting the vessel, rigidly interconnects an upright internal lid and two upright external lids which are axially separated by a distance corresponding to the spacing of the two end flanges of the vessel, the internal lid coming to rest against one or the other inner seat while a respective external lid lies against the opposite outer seat to seal the vessel, the development of steam pressure within the vessel exerting upon these lids a differential force holding them firmly in their closure position. Upon the venting of the vessel, the carriage can be shifted with introduction of a fresh load into the vessel and removal of the one previously treated. In a simplified embodiment, one of the two external lids is omitted.

10 Claims, 8 Drawing Figures

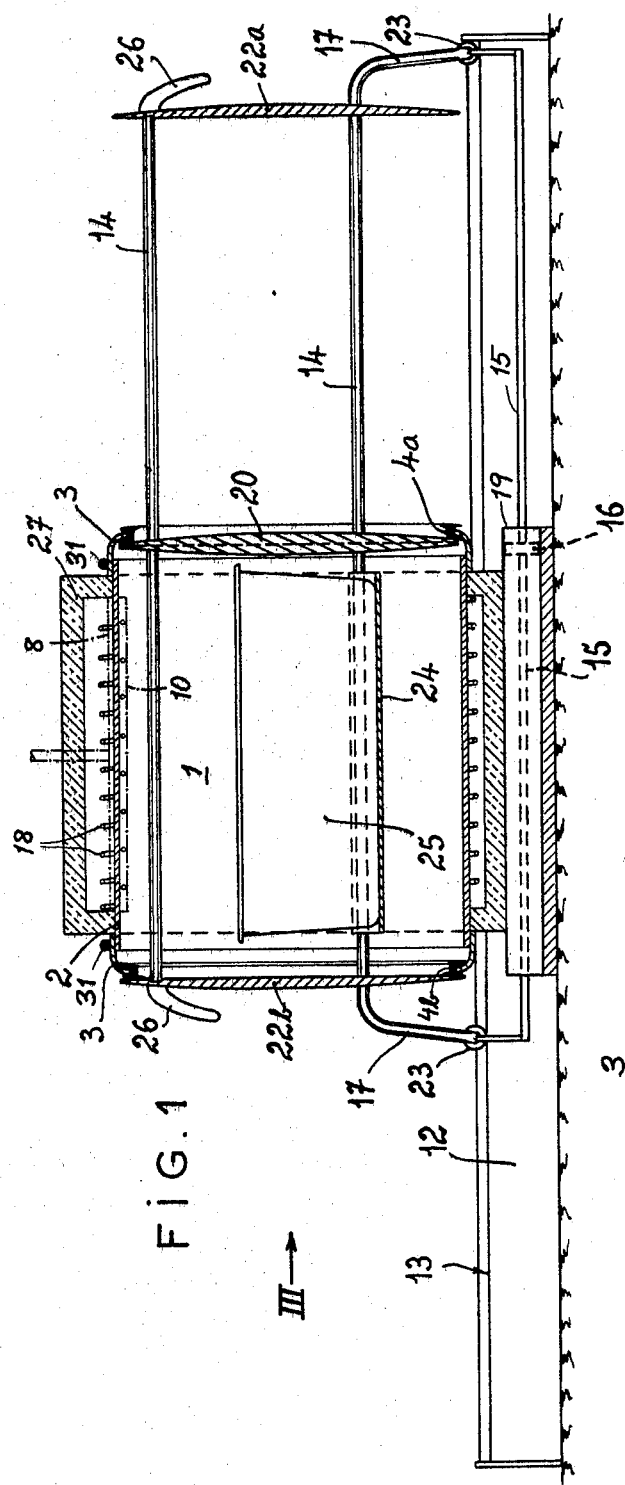
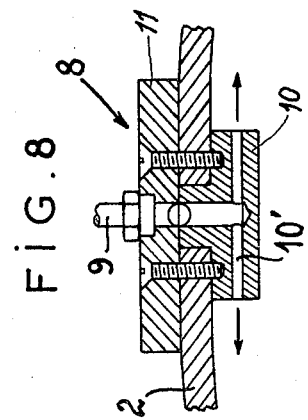
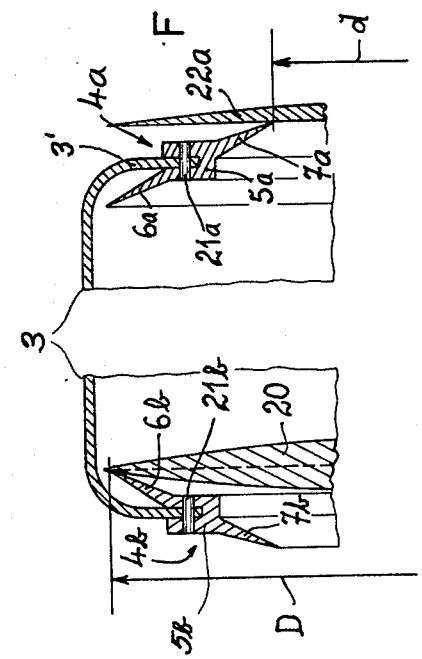

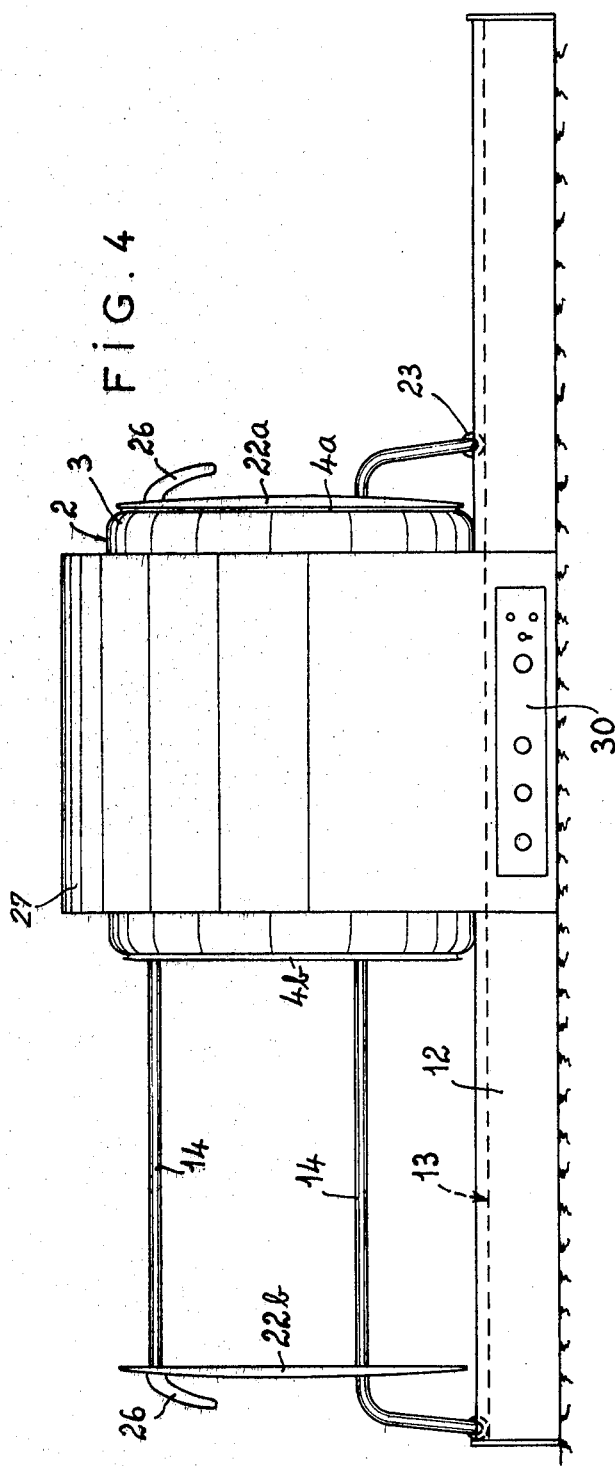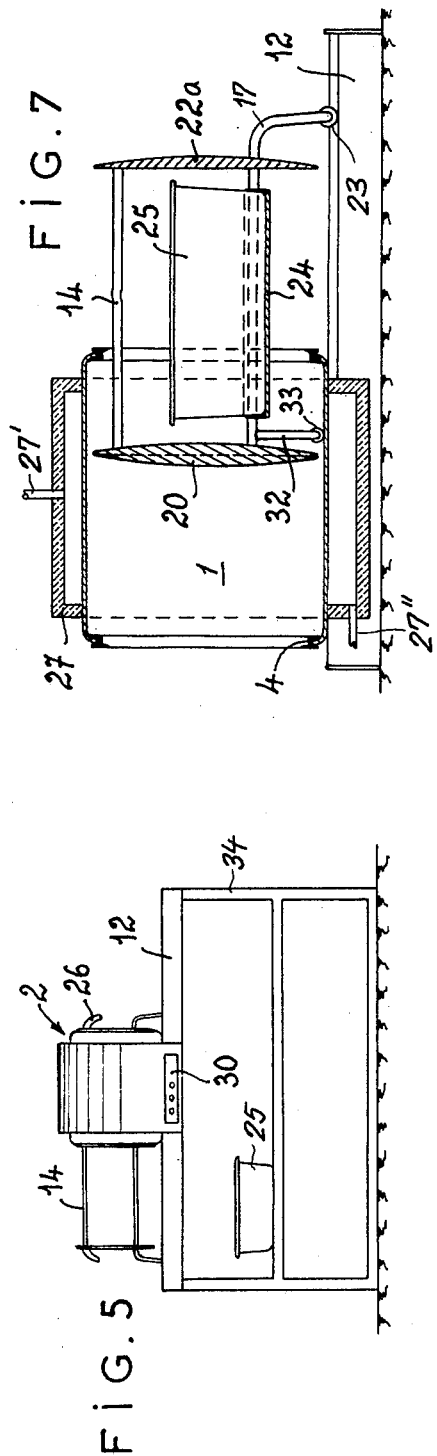

AUTOCLAVE

FIELD OF THE INVENTION

My present invention relates to an appliance, known as an autoclave, to be used as a pressure cooker or a sterilizer for the steaming of foods, garments or other articles.

BACKGROUND OF THE INVENTION

In facilities using such appliances, e.g. restaurant kitchens or hospitals, a number of autoclaves are often installed in somewhat crowded quarters creating difficulties of access and personal safety. Thus, conventional autoclaves have vessels with hinged lids which are swung out for the introduction and the removal of a load and which in their open position tend to encroach upon passageways used by the operating personnel. Furthermore, a premature opening of the vessel exposes the operator to the danger of scalding by steam still present in its treatment chamber. Even when that chamber has been properly vented, the goods inside are still hot and can therefore be handled only with difficulty.

Devices are known which prevent the opening of an autoclave as long as its internal pressure exceeds a certain threshold. These safety devices, however, are generally cumbersome and their mere presence may make the operating personnel apprehensive.

OBJECTS OF THE INVENTION

The general object of my present invention, therefore, is to provide an autoclave of simple construction which obviates all the aforestated drawbacks.

A more particular object is to provide an appliance of this kind which can be rapidly unloaded and reloaded in a safe and efficient manner.

SUMMARY OF THE INVENTION

These objects are realized, in accordance with my present invention, by providing a vessel (preferably in the form of a horizontal cylinder) which forms a treatment chamber having two open ends, the peripheral vessel wall terminating at these ends in a pair of inwardly projecting annular shoulders lying in parallel planes. A carriage displaceable perpendicularly to these planes extends partly into that chamber and forms a support for goods to be treated. A first and a second lid, parallel to the shoulders of the vessel wall, are fixedly mounted on the carriage inside and outside the treatment chamber, respectively. In an extreme carriage position, the first lid closes one of the two chamber ends by coming to rest against an inner seat on the corresponding shoulder while the second lid simultaneously closes the other end by abutting an outer seat of the opposite shoulder whereby the chamber is sealed, the support for the goods lying between these lids so as to be inside the chamber in that position. When steam is admitted into or generated within the treatment chamber, its pressure acts differentially upon the two lids to intensify their contact with the respective shoulders inasmuch as the inner seat surrounds an area larger than that surrounded by the outer seat. Thus, the carriage is firmly held in its closure position until the internal steam pressure has so far abated that the carriage may be moved into its alternate position, automatically or by hand, to extract the treated goods from the chamber preparatorily to a reloading thereof.

In a particularly advantageous embodiment, a third lid parallel to the other two is also fixedly mounted on the carriage outside the treatment chamber, opposite the second lid, to come to rest against the opposite seat of the first-mentioned shoulder while the first lid engages an inner seat on the opposite shoulder so that the chamber is sealed in both extreme carriage positions. In each of these positions, a goods-supporting portion of the carriage is exposed to give access to the load previously treated and to facilitate the emplacement of a new load to be treated in the next cycle.

Especially in a symmetrical embodiment of the type last described, the shoulders at the chamber ends can be formed by inbent rims of the peripheral wall, the inner edge of each rim being reinforced by a ring having an axially inwardly diverging flange and an axially outwardly converging flange defining the inner and outer seats, respectively. These flanges preferably constitute resilient lips with pointed cross-sections lying substantially in line with each other so that approximately the same reaction forces are encountered by the inner lid and one of the outer lids at opposite ends of the chamber in the final stage of closure.

BRIEF DESCRIPTION OF THE DRAWING

The above and other features of my invention will now be described in detail with reference to the accompanying drawing in which:

FIG. 1 is a longitudinal sectional view of an autoclave embodying my invention;

FIG. 2 is a sectional detail view, drawn to a larger scale, of parts of the autoclave shown in FIG. 1;

FIG. 4 is an elevational view of the autoclave of FIG. 1, shown in an alternate position;

FIG. 5 is a view similar to FIG. 4 but drawn to a smaller scale, showing the autoclave installed on a rack;

FIG. 7 is an elevational view similar to FIG. 1 but showing a simplified autoclave according to my invention; and FIG. 8 is a cross-sectional view, drawn to a larger scale, of a constructional detail.

SPECIFIC DESCRIPTION

Figure 6:
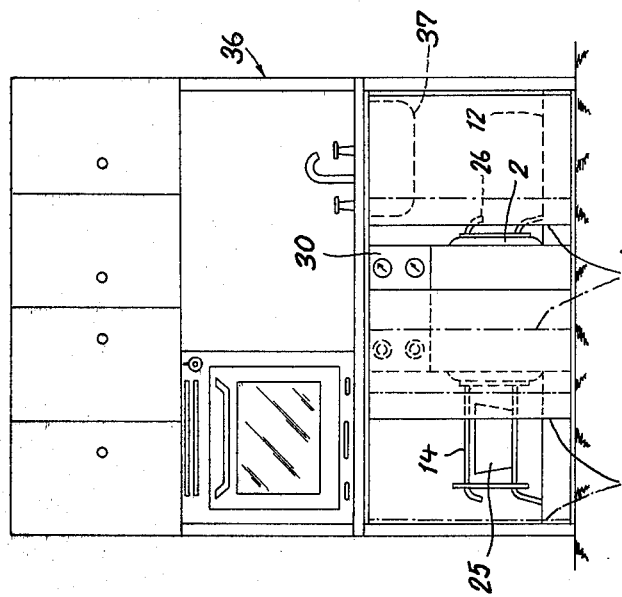
FIG. 6 is an elevational view of a kitchen cabinet provided with the autoclave of FIGS. 1 – 4.

In FIGS. 1 – 4 I have shown an autoclave comprising a cylindrical vessel 2 centered on a horizontal axis defining a treatment chamber 1 open at both ends, the peripheral wall of the vessel terminating in a pair of end caps 3 with inbent rims 3' which form part of a pair of annular shoulders 4a, 4b. Each shoulder has an annular core 5a, 5b, embracing the corresponding rim 3' as a reinforcing ring therefor, which is integral with two annular flanges designed as resilient lips, i.e. an axially inwardly diverging flange 6a, 6b and an axially outwardly converging flange 7a, 7b. Each core 5a, 5b is held in position on the associated rim 3' by a set of pins 21a, 21b (only one shown).

Figure 3:
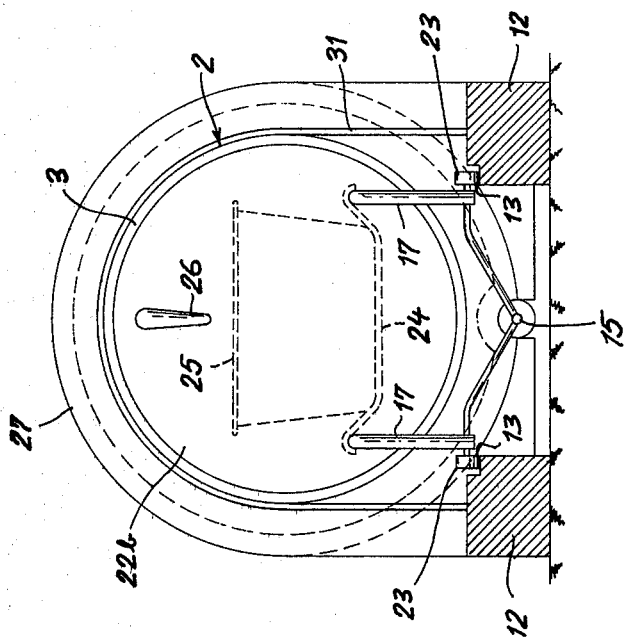
FIG. 3 is an end view taken in the direction III of FIG. 1.

The free edge of each flange 6a, 6b forms an inner seat for a central lid 20 which is a disk with two convex faces and is held captive within chamber 1 by the two end caps 3. Conversely, the free edges of flanges 7a, 7b form outer seats for a pair of external lids 22a, 22b which symmetrically flank the central lid 20 and have flat faces confronting each other. The three lids 20, 22a and 22b are rigidly interconnected by a carriage 14 designed as a framework for the support of goods to be treated, such as a pan 25 resting on a removable tray 24 as seen in FIGS. 1 and 3. Carriage 14 terminates beyond each external lid in a pair of legs 17 bearing rollers 23 that ride on tracks 13 of a base 12 on which the vessel 2 is mounted with the aid of straps 31. The axial separation of lid 20 from either lid 22a, 22b substantially equals the spacing of the two shoulders 4a, 4b whereby one of these external lids 22a or 22b abuts the outer flange 7a or 7b of one shoulder whenever the central lid 20 comes to rest against the inner flange 6b or 6a of the opposite shoulder, as is the case in the two extreme carriage positions respectively illustrated in FIGS. 1 and 4. In each of these limiting positions, a tight joint is formed between the shoulders 4a, 4b and the lids 20 and 22a or 22b respectively in contact therewith; at the same time, a portion of carriage 14 remains accessible for the removal of a load previously deposited thereon and the emplacement of a new load to be subsequently introduced into chamber 1.

As particularly indicated in FIG. 2, the inner seats formed by the edges of flanges 6a, 6b have a diameter D substantially exceeding the diameter d of the outer seats formed by the flanges 7a, 7b. With the chamber closed in either of the limiting positions referred to, steam pressure generated inside chamber 1 will exert a larger force upon lid 20 than upon lid 22a or 22b whereby the carriage is strongly biased in a direction of closure (to the left in FIG. 2) so that the joints between these lids and the respective shoulders are tightly sealed.

Vessel 2 is shown encased in a jacket 27 provided with an electric heater 18 designed to vaporize water introduced into the chamber 1 together with the load or in some other way, e.g. through a distributor 8 optionally provided therein as indicated in dot-dash lines in FIG. 1; naturally, other conventional heating means (e.g. a steam jacket as described below with reference to FIG. 7) could also be used. In FIG. 8 the distributor 8 is shown as comprising a manifold 10 and a backing strip 11 between which confronting edges of the peripheral wall of vessel 2, formed from sheet metal, are clamped. Manifold 10 has outlets 10' communicating with a conduit 9 through which water can be admitted, either for the generation of steam or for rinsing grease or the like off the inner wall surface of the vessel. A control panel 30 (FIG. 4) has knobs for regulating the water supply and adjusting the operating temperature. The vessel may also be provided with one or more valves (not shown) for releasing the generated steam.

Whenever the internal pressure of the vessel has been sufficiently reduced, either by cooling or by venting, the carriage 14 may be shifted into its alternate position to start a new cycle. For this purpose, each external lid 22a, 22b is shown provided with a handle 26 enabling a manual changeover. The carriage may also be automatically reciprocable with the aid of suitable drive means here shown as a fluidically operated jack including a double-acting piston 16 in a cylinder 19, two piston rods 15 being secured to opposite ends of the carriage. The actuation of the jack can be controlled by an operator, with the aid of panel 30, or in a fully automated manner via a nonillustrated programmer or timer as is well known per se.

In FIG. 5 the base 12 has been shown incorporated in a rack 34 serving for the storage of utensils such as pan 25.

In FIG. 6 I have illustrated a cabinet 36 with the usual kitchen equipment, including a sink 37, having a lower compartment which accommodates an autoclave of the type described with reference to FIGS. 1 – 4. This compartment has two sliding doors 35, 35' which can give access to the left-hand or the right-hand end of the appliance for the insertion and the removal of loads such as pan 25.

As illustrated in FIG. 7, the autoclave according to my invention can be simplified by the omission of one of the two external lids (here the left-hand lid 22b) and a corresponding foreshortening of the carriage 14; in this instance, the carriage has only one pair of outer legs 17 with rollers 23 while the other pair is replaced by a single leg 32 inside chamber 1 having a roller 33 which rides on the bottom of the vessel. Here, of course, the chamber 1 remains open when the carriage is shifted to the right for the replacement of one load by another. By way of example, jacket 27 is shown provided in FIG. 7 with an inlet 27' and an outlet 27" for an external heating fluid such as superheated steam.

Since only the inner flange 6b of the left-hand shoulder 4b and the outer flange 7a of the right-hand shoulder 4a (see FIG. 2) are operative in the appliance of FIG. 7, their other two flanges 7b and 6a could be omitted.

As will be apparent from the foregoing description, my improved autoclave is of compact design and does not have any transversely projecting parts which could interfere with traffic alongside its base 12. In an automated system with a plurality of symmetrical appliances of the type shown in FIGS. 1 – 6 juxtaposed on a common base 12, their synchronized operation will allow a reduction of the separation of their vessels 2 to a distance exceeding only slightly the stroke length of their carriages 14.

I claim:

1. An autoclave comprising:
   a vessel forming a treatment chamber with two open ends, said vessel having a peripheral wall terminating at said ends in a pair of inwardly projecting annular shoulders lying in parallel planes;
   a carriage displaceable perpendicularly to said planes, said carriage extending partly into said chamber and forming a support for goods to be treated therein;
   a first lid parallel to said shoulders fixedly mounted on said carriage within said chamber for closing one of said ends by abutting an inner seat on the corresponding shoulder in one extreme carriage position;
   a second lid parallel to said shoulders fixedly mounted on said carriage outside said chamber for closing the other of said ends by abutting an outer seat on the shoulder thereof upon said first lid abutting the opposite shoulder in said one extreme carriage position, thereby sealing said chamber, said support being located between said lids; and
   control means for generating steam pressure in the chamber thus sealed, said inner seat surrounding an area larger than that surrounded by said outer seat whereby said steam pressure acts differentially upon said lids to intensify their contact with the engaged seats and prevent a shifting of said carriage during treatment of the goods in said chamber.

2. An autoclave as defined in claim 1 wherein said carriage projects from both ends of said chamber, further comprising a third lid parallel to said shoulders fixedly mounted on said carriage outside said chamber opposite said second lid for closing said one of said ends by abutting an outer seat on the shoulder thereof upon said first lid abutting the shoulder of said other of said ends in another extreme carriage position, said carriage being externally loadable in each extreme position with goods to be treated in the opposite extreme position.

3. An autoclave as defined in claim 2 wherein said shoulders are formed by inbent rims of said peripheral wall, the inner edge of each rim being provided with a reinforcing ring, said inner seat being formed by an axially inwardly diverging flange on said reinforcing ring, said outer seat being formed by an axially outwardly converging flange on said reinforcing ring.

4. An autoclave as defined in claim 3 wherein said inwardly diverging and outwardly converging flanges constitute resilient lips with pointed cross-sections substantially in line with each other.

5. An autoclave as defined in claim 1 wherein said planes are vertical, said vessel being provided with a horizontal base forming a track for the guidance of said carriage.

6. An autoclave as defined in claim 5 wherein said carriage has wheels riding on said track.

7. An autoclave as defined in claim 5 wherein said peripheral wall is cylindrical and provided at its top with an inlet for the admission of water into said chamber.

8. An autoclave as defined in claim 1, further comprising drive means for automatically reciprocating said carriage between said extreme positions thereof.

9. An autoclave as defined in claim 8 wherein said drive means comprises a fluidically operated piston linked with said carriage.

10. An autoclave as defined in claim 1, further comprising handle means on an outer surface of said second lid.

* * * * *